US008628466B2

United States Patent
Orten et al.

(10) Patent No.: US 8,628,466 B2
(45) Date of Patent: Jan. 14, 2014

(54) METHOD AND MEANS FOR ERECTION ENHANCEMENT

(75) Inventors: Birger Orten, Drammen (NO); Lasse Werner, Drammen (NO); Fredrik Askjem, Drammen (NO)

(73) Assignee: Orbus AS, Drammen (NO)

( * ) Notice: Subject to any disclaimer, the term of this patent is extended or adjusted under 35 U.S.C. 154(b) by 120 days.

(21) Appl. No.: 13/129,701

(22) PCT Filed: Nov. 23, 2009

(86) PCT No.: PCT/NO2009/000400
§ 371 (c)(1),
(2), (4) Date: Jul. 29, 2011

(87) PCT Pub. No.: WO2010/059064
PCT Pub. Date: May 27, 2010

(65) Prior Publication Data
US 2011/0288370 A1 Nov. 24, 2011

(30) Foreign Application Priority Data
Nov. 21, 2008 (NO) .................................. 20084904

(51) Int. Cl.
*A61F 5/00* (2006.01)
(52) U.S. Cl.
USPC .............................................. 600/38; 601/46
(58) Field of Classification Search
USPC .................................. 600/38–41; 601/46–49
See application file for complete search history.

(56) References Cited

U.S. PATENT DOCUMENTS

| 4,966,131 | A | 10/1990 | Houghton et al. |
| 5,095,890 | A | 3/1992 | Houghton et al. |
| 2005/0283044 | A1* | 12/2005 | Chang ............................. 600/38 |
| 2007/0038019 | A1* | 2/2007 | Weng .............................. 600/38 |
| 2009/0306468 | A1* | 12/2009 | Tasker et al. .................... 600/41 |
| 2009/0318755 | A1* | 12/2009 | Adams et al. ................... 600/41 |

FOREIGN PATENT DOCUMENTS

| CL | 200503013 | 11/2005 |
| WO | 9209962 A1 | 6/1992 |
| WO | 0170150 A1 | 9/2001 |

(Continued)

OTHER PUBLICATIONS

Bovenzi, M., et al., "Response of Finger Circulation to Energy Equivalent Combinations of Magnitude and Duration of Vibration," Occup. Environ. Med. 2001; 58:185-193 (10 p.).
Skoglund, C.R., "Vasodilation in Human Skin Induced by Low-Amplitude High-Frequency Vibration," Clinical Physiology (1989) 9, 361-372 (12 p.).
PCT/NO2009/000400 International Search Report, Feb. 19, 2010 (3).

(Continued)

*Primary Examiner* — John Lacyk
(74) *Attorney, Agent, or Firm* — Conley Rose, P.C.

(57) ABSTRACT

A means for achieving enhanced erection includes a mounting attachment (10) to be placed onto the penis, e.g. in the form of a penis ring of a substantially elastic material. On the mounting attachment (10), one or more rows (14) of miniature vibrator motors (8 ABC) is/are provided, each row comprising at least three motors. For sequential pulsating operation of the motors (8 ABC) of the row(s) (14), an electric power supply arrangement (7) and an electronic control circuit (9) are provided. The control circuit (9) and the power supply arrangement (7) may be positioned on the mounting attachment (10). In one embodiment, piezoelectric foil strips (15 *abc*) are located underneath the vibrator motors (8 ABC) and are operated in a controlled relation to the motor operation for generating mechanical vibrations with a frequency that is higher than the frequency of the vibrator motors.

23 Claims, 6 Drawing Sheets

(56) References Cited

FOREIGN PATENT DOCUMENTS

| WO | 03037242 A2 | 5/2003 |
| WO | 2004110320 A1 | 12/2004 |
| WO | 2007105248 A1 | 9/2007 |

OTHER PUBLICATIONS

Search Report for Norwegian Application No. 20084904, Apr. 14, 2009 (2 p.).
Office Action for Chilean Application No. 2011-001139 dated Dec. 27, 2012 (6 p.).

* cited by examiner

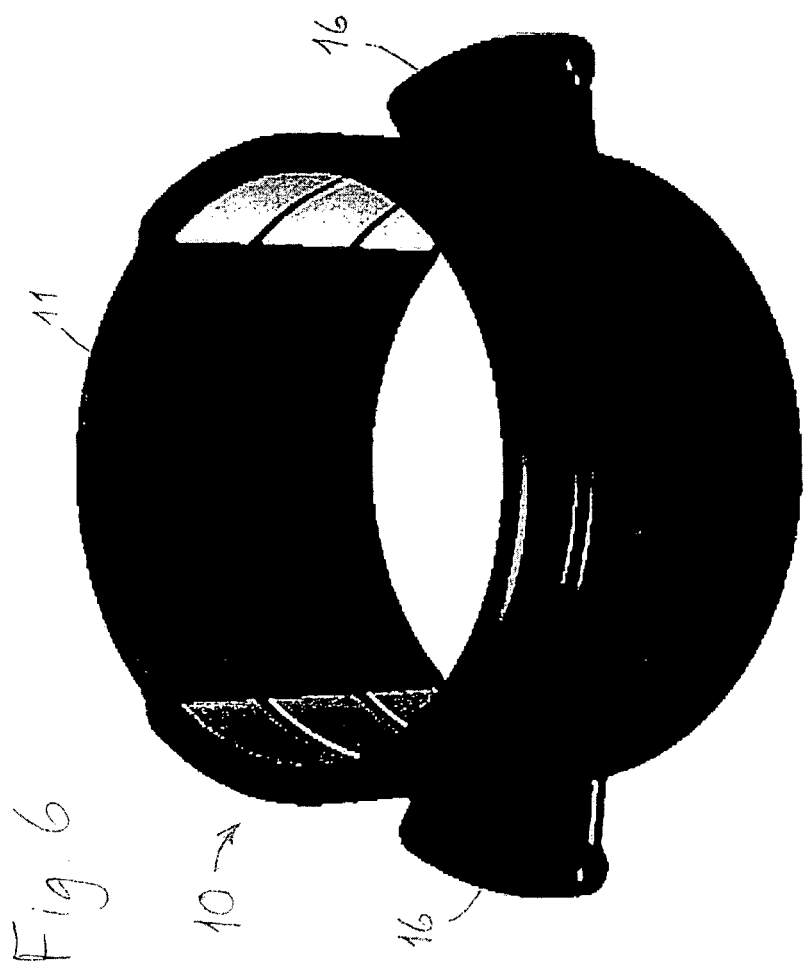

METHOD AND MEANS FOR ERECTION ENHANCEMENT

CROSS-REFERENCE TO RELATED APPLICATIONS

This application is a 35 U.S.C. §371 national stage application of PCT/NO2009/000400 filed Nov. 23, 2009, which claims the benefit of Norwegian Application No. 20084904 filed Nov. 21, 2008, both of which are incorporated herein by reference in their entireties for all purposes.

STATEMENT REGARDING FEDERALLY SPONSORED RESEARCH OR DEVELOPMENT

Not applicable.

BACKGROUND AND PRIOR ART

The present invention relates to methods and means for providing for or at least assisting in the provision of an erected state of the male sex organ. This may be desirable in the case of an erectile dysfunction, but also finds application for persons with a normal erectile function as an additional stimulation in sexual contexts.

In normal cases, an erection can be achieved by mechanical stimulation, manually or by the use of a vibrator means, by chemical stimulation, or simply by psychological influence.

However, in the case of more special medical indications, such as a full paralyzation or various severe physical or psychological conditions, the ability to achieve an erection may be strongly reduced or even entirely absent. In such cases the only possibility for achieving an erection may be a vibrator means or chemical influence, typically through injection or intake of tablets. Often, a vibrator means will be a preferred solution, because injections are associated with pain and intake of tablets often brings along significant side effects, both for normally fit and highly impaired persons.

At some treatment institutions a vibrator plate is used on which the penis is placed, but such equipment is unnecessary large and difficult to handle.

Condoms having a "vibrator" mounted thereon, intended to "do it for both parts at the same time," are available in the market, presumably as a general stimulation or as an additional amusement. The vibrator is a small electro motor with a skew or eccentric load on a rotating axle. Also available are "penis rings" with a similar vibrator motor, i.e. which does not have the function of retaining any ejaculated sperm, but wherein the function of the ring is to maintain the erection by preventing backflow of blood from the penis.

An example of such a penis ring is disclosed in the international publication WO 03/037242. In this publication, a so-called "penis vibrator" is described that is intended to stimulate both the male and female sex organs during sexual intercourse. The penis vibrator of WO 03/037242 is comprised of a ring or a ring-shaped band that has an outward bulb, and to the bulb a small "micro vibrator unit" as well as a battery unit are attached. The battery unit is equipped with a starting arrangement in the form of a rotary sleeve, which when turned makes contact with the battery and closes the electrical circuit to the vibrator unit. The manner of operation is that the vibrator is started by rotating the rotary sleeve and then runs until the battery is empty, or until it is switched off by an opposite rotation.

The most closely related prior art is found in WO 2007/105248, which like WO 03/037242 is a penis ring for imparting stimulating mechanical vibrations to both the male and female sex organs during intercourse. The difference relative to WO 03/037242 is that in WO 2007/105248, a ring comprising two micro vibrator units is disclosed and shown. One unit is meant for stimulating the penis, whereas the other is meant for stimulating the vagina. In one embodiment, the two vibrator units are arranged in parallel, but at opposite sides or "ends" of the penis ring carrying them.

A click button starting mechanism is provided for each vibrator unit, enabling the continuous operation of each vibrator until the associated battery runs empty, or until the click button is actuated to the stop position.

WO 1992/09962 describes an apparatus for sensing and measuring penile blood flow and erectile function using piezoelectric elements.

For many years, ultrasound power systems have been used for physical therapy in the treatment of sore muscles and other ailments. Such systems preferably operate in the range 1-3 MHz, which range is known to have an effect on the circulation of blood. For example, U.S. Pat. Nos. 4,966,131 and 5,095,890 to Mettler Electronics describe different elements in a hand held device for such treatment.

It is also known that at frequencies in the range 150-250 Hz, low amplitude vibrations (10-25 µm) causes expansion of the blood vessels in the skin, whereas higher amplitudes (100-200 µm) in the same frequency range causes the blood vessels to contract. See C R Skoglund: "Vasodilatation in human skin induced by low-amplitude high-frequency vibration", Clinical physiology, 1989 August; 9(4):361-72. A study by Bovenzi et al ("Response of finger circulation to energy equivalent combinations of magnitude and duration of vibration", Occupational and Environmental Medicine, 2001 March; 58(3):185-93) shows that vibrations at 125 Hz can reduce the blood flow in the skin, and that the reduction of blood flow is greater with longer times of exposure. The results from Bovenzi et al seem consistent with the high amplitude results of Skoglund referenced above.

The aim of the present invention is primarily to assist in achieving, enhancing, and maintaining a penis erection, and to a lesser extent to also stimulate a sex partner. However, in certain scenarios such an effect could also be attained using the method and means according to the present invention.

In addition to focusing on influencing only the male sex organ, the present invention takes as a point of departure, that the effect obtained using a vibrator penis ring according to the prior art will be insufficient for many people. There is hence a need for a stronger and more efficient activation of penis.

The present invention is conceived to meet the above need. Thus, according to the invention, an erection enhancement method as defined in the appended claim 1 is provided, as well as an erection enhancement means as defined in the appended claim 14. Preferred and favorable embodiments of the invention will be apparent from the appended dependent claims.

The invention is based on the knowledge that pro-erectile activation may be increased by providing vibrating massage along the penis, so that the blood flow to the penis is stimulated.

BRIEF DESCRIPTION OF THE DRAWINGS

In the following description, exemplary embodiments of the present invention will be discussed in more detail with reference to the attached drawings, in which:

FIG. 6 shows a safety feature recommended on the means according to the invention.

DETAILED DESCRIPTION OF A PREFERRED EMBODIMENT

The lack of erection with men is a well-known problem. The reason may be of a physical as well as a psychological nature. In some cases healing may be achieved, i.e. the patient regains a normal erectile function.

In other cases such healing is not possible, and a next best solution is to make erection possible despite the underlying problem. It is then necessary with some kind of "intervention" or assistance so that an erection is achieved in a crucial time period, typically when performing sexual intercourse.

In special cases of severely disabled persons, a therapist may provide assistance in achieving an erection and possibly having an ejaculation, either by the injection of a chemical substance or by the use of a mechanical aid, as mentioned above.

In one aspect, the present invention is directed towards the latter scenario, but is also aimed at providing an efficient means, of a non-chemical type, of self-help and for use by healthy persons that feel the need for additional stimulus in their sex life.

Like the prior art described above, the means according to the present invention is based on the use of small vibrator units. Such vibrator units are comprised of a small DC motor with an eccentrically positioned weight on the motor axle, so that when the motor is supplied with power and rotates the axle, mechanical vibrations having the same frequency as the rotational frequency of the motor are generated. Such vibrator motors are commercially available as very small units, commonly having a length of less than 1 cm and having a diameter as small as 3 mm. Among the manufacturers of such small vibrator units can be mentioned Shicoh Co. Ltd. and Namiki Seimitsu Honseki K. K., both of Japan.

Motor speeds, i.e. rotational frequencies, will be in the range of 50-200 Hz. The motors may be powered by a DC voltage in the range of 1-5 volts, and are possible to energize using small batteries.

Figure 1:
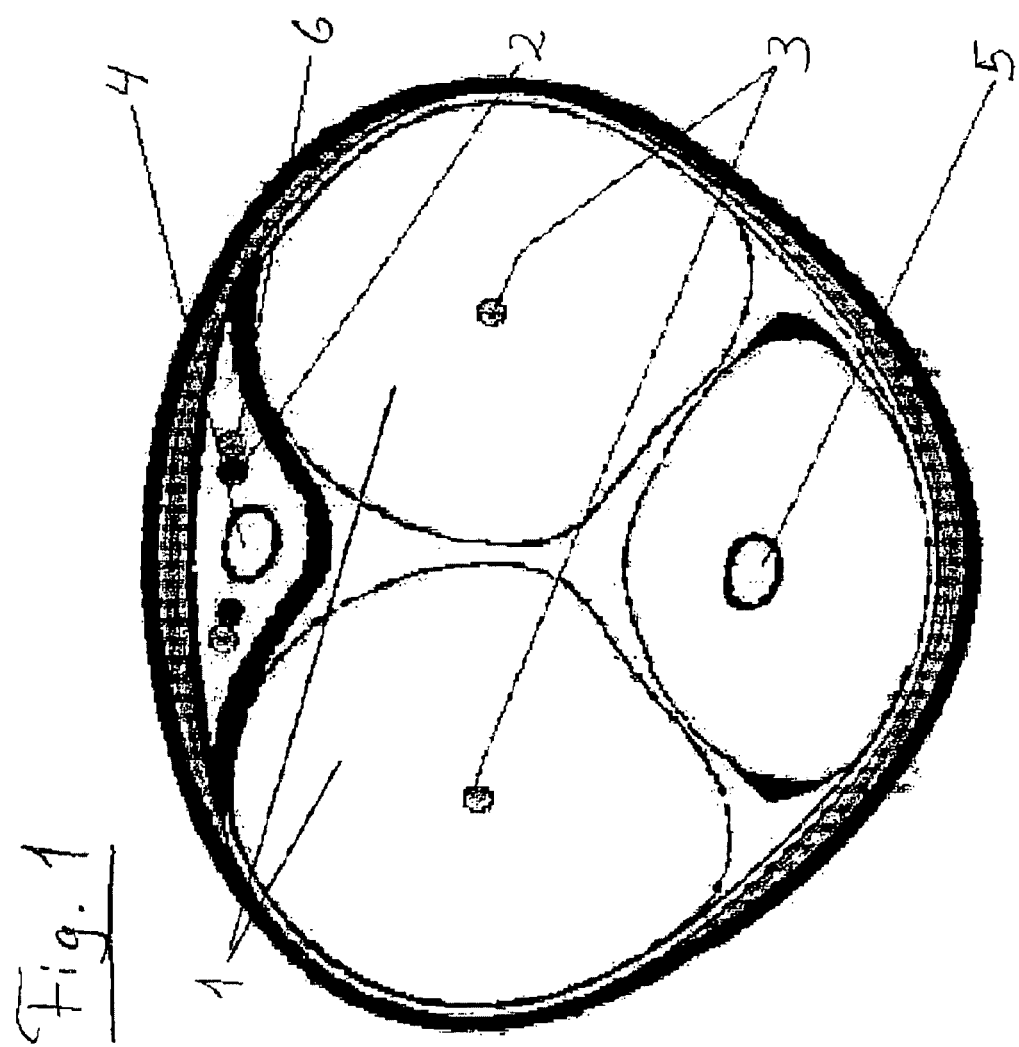
FIG. 1 shows a cross-section of the male sex organ.

In order to better explain the invention, it will be beneficial to examine in more detail the inner structure of the penis, and it is therefore referred to FIG. 1, showing a cross-section perpendicular to the longitudinal direction of the penis. The figure shows the two sponge bodies 1 that on an erection are filled with blood, arteries 2 and 3 that supply blood, a vein 4 that leads blood back, the urethra 5, and nerves 6.

It is desirable to enhance the erection by stimulating the nerves 6 through the application of mechanical vibrations, similar to what is achieved by the prior art. However, in order to further enhance the erection, the idea is now to influence the blood flow out to the sponge bodies 1 by massaging using "traveling vibrations", especially in the upper area in which arteries 2 and vein 4 are located. A forward-propagating vibration will act to increase the in-flow of blood, and less blood will exit penis while the outwardly directed massage is proceeding.

Figure 2:
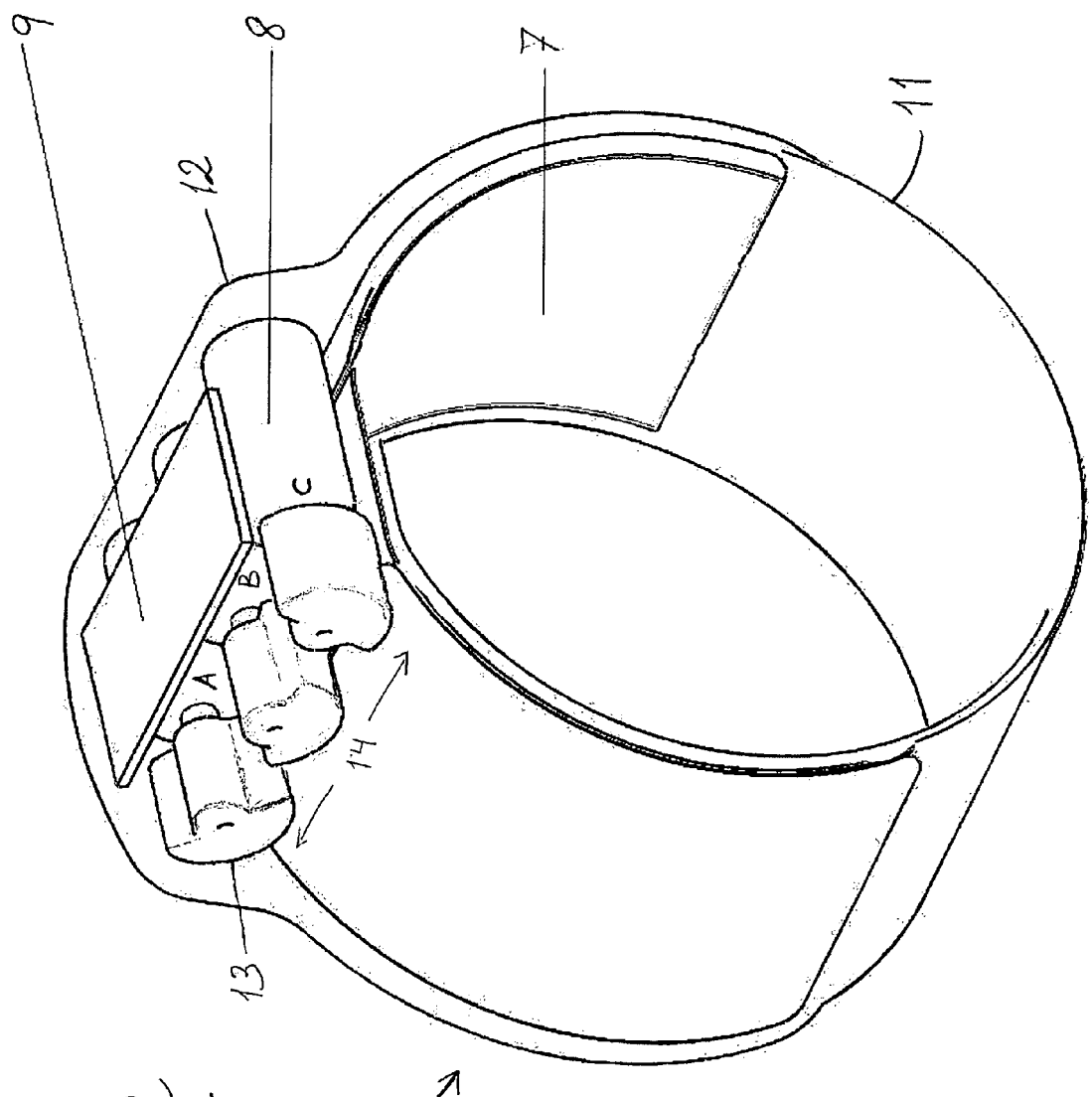
FIG. 2 shows a basic embodiment of a means according to the present invention.

In order to effect such massage as mentioned above, as a first and non-limiting example or embodiment of the invention, a mounting attachment 10 for vibrator units is provided, in the form of a penis ring such as shown in FIG. 2. Basically, penis ring 10 comprises a ring 11 of an elastic material, such as rubber, silicon, or allergy-tested latex material, for example. The lower part of ring 10 is advantageously free of other equipment, so that an open rubber area is ready to stretch in order to allow for the expansion necessary when the penis is erecting.

When the expressions "top," "bottom," "on the sides" are used herein, these are relative to the normal position in which the ring, or more generally the mounting attachment, is recommended to be mounted. The user will be instructed that the correct positioning is with vibrator motors 8 on the upper side of penis (which is then envisioned being in a substantially horizontal position, on a user standing up). With this, the directions/position should be defined.

Penis ring 10 is equipped with a row 14 of vibrator motors 8 (three motors, A, B, C, in the example shown), a battery 7, and an electronic control circuit 9. In this example, battery 7 is shown as a so-called "paper battery" that may be positioned so as to follow and extend along the surface of the ring, either embedded into or on the inside of the ring. Moreover, the battery arrangement may be configured in various suitable manners, e.g. with small disc-shaped or cylindrical batteries nearby the vibrator units. Also, in some embodiments, electric power may be supplied via cable from an external power source, and the control circuit may similarly be positioned outside of mounting attachment 10. Such an embodiment is particularly suited for institutionalized patients.

Wires (not shown) connect battery 7, the electronic control circuit 9, and vibrator motors 8 in the embodiment of FIG. 2. A start button or switch is advantageously positioned on the side of the elevation 12 into which the vibrators and circuit are cast. (In an embodiment having external power and control, start/stop will also advantageously be operated externally.) It is noted that the drawing of FIG. 2 is schematic and a principle drawing. The unbalanced flywheels 13 of the miniature motors are hence able to rotate freely, i.e. they are located in separate chambers (not shown).

In a more sophisticated embodiment, the penis ring/mounting attachment includes, preferably on the underside of the vibrator/controller assembly, a sensor assembly for capturing the heart beat frequency (pulse) of the user, either by passive listening at the arteries 2 on top of the penis, or in a more advanced manner using ultrasound and Doppler echo measurement of the blood flow. The reason for sensing the heart rate of the user is to adjust the intensity of the vibratory impact to the current physical condition of the user, for which the heart activity is a good indicator. The adjustment may then be accomplished through a regulation of the operational scheme of the vibrators, typically by varying the length and occurrence rate of intermittent breaks (see below). The speed of the vibrator motors may also be regulated. In a more sophisticated embodiment, it is also possible to embed an erection sensor sensing the strength of the erection, e.g. using a technology similar to the RigiScan technology (see below), or through a simple pressure measurement on the inside of the ring. Adjustment of the operating scheme may also be carried out in dependency of such measurements.

As compared to the design shown in FIG. 2, some variants are possible:

Firstly, the number of vibrator units 8 may be increased to four, five, or more. Preferably however, such motors should form a linear row 14 as shown in FIG. 2.

It is also possible to enhance the activation further by providing similar vibrator rows on the sides, preferably symmetrically with an additional row on each side located approximately 60-90° down from the top. In this case, it is also possible to massage-activate the arteries 3 (see FIG. 1).

A further extended embodiment results from providing an additional two rows further down on the periphery, so that five vibrator rows are distributed around the periphery, with the first row being "on top" of the periphery. It was mentioned above that a lower part of ring 10 advantageously should be free of "equipment" in order to form an area of expansion, but in the present example with a greater number of vibrator rows, each area between the vibrator rows should be such expansion areas.

In one embodiment the top vibrator row is omitted, so that the main objective becomes to activate the arteries in sponge bodies 1 using four vibrator rows on the sides, for example. The uppermost ones of four such vibrator rows will also ensure an adequate influence on the nerve bundles 6.

Figure 3:
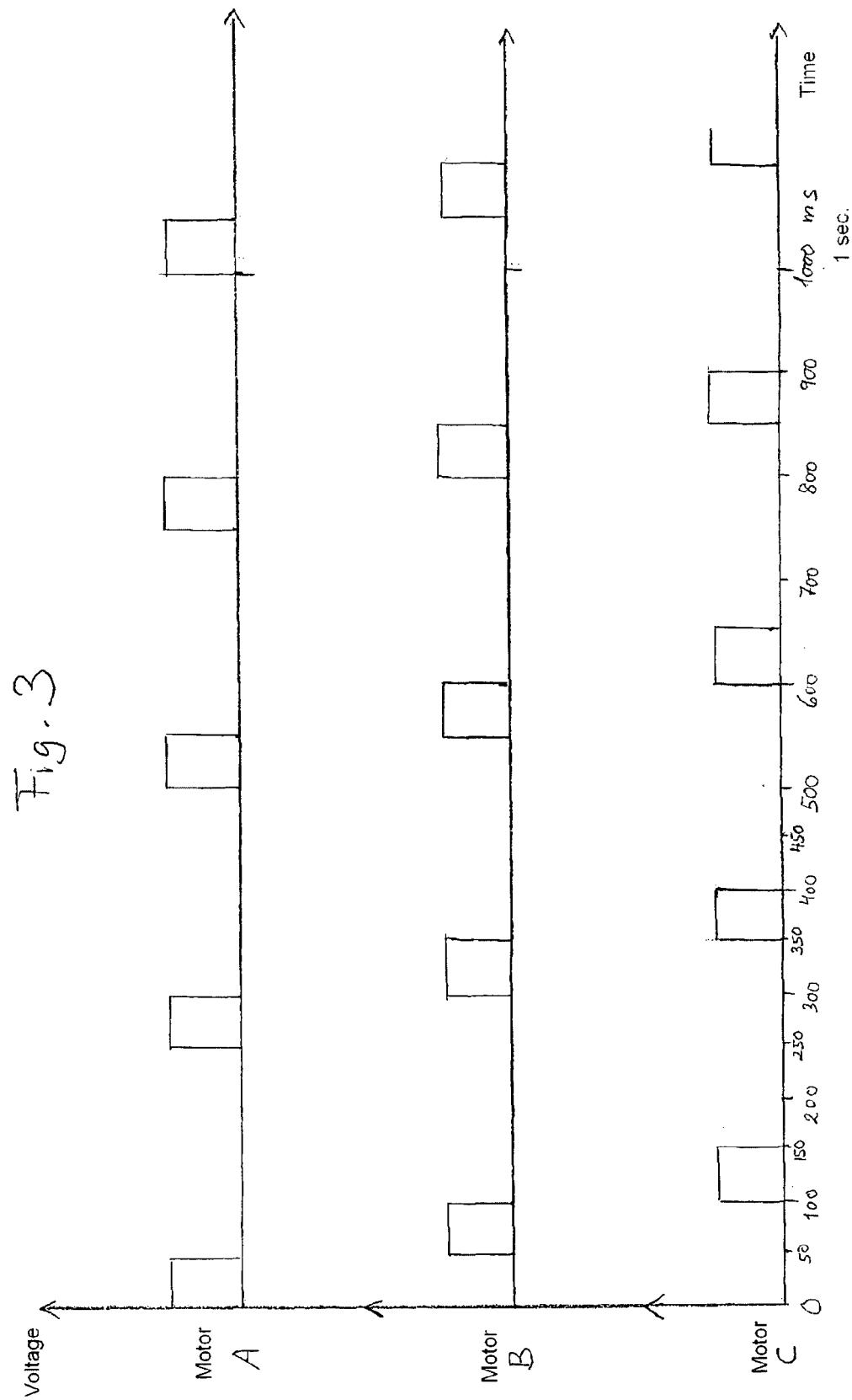
FIG. 3 shows an exemplary operating scheme for use by the means shown in FIG. 2.

Exemplary modes of operation for the means according to the invention will be described in the following. In the simple exemplary embodiment shown in FIG. 2, a major idea is that the vibrator units 8 A, B, C are to be operated sequentially starting closest to the root of the penis (assumed on the left in the figure), in order to generate an outwards massaging movement in the lengthwise direction of the penis. Each vibrator unit 8 typically rotates with a rotational frequency in the range of 50-200 Hz. It is here assumed a vibrator frequency of 80 Hz. Reference is made to FIG. 3, which shows a scheme for operating the motors/vibrators:

From time zero electrical actuating power is supplied to motor A (nearest the root of the penis) for a time period of 50 ms, followed by a break of 200 ms. Then actuating power is supplied to motor B from time 50 ms to time 100 ms, followed by a pause of 200 ms. Then motor C is run from time 100 ms to time 150 ms, followed by a break of 200 ms. Then motor A is rerun from time 250 ms to time 300 ms followed by a break of 200 ms, after which all three motors are run in cyclic operation for a working period of 60 seconds. Accordingly, a sequential pulsation of the three motors takes place during this working period. It should be noted that one motor may start before the previous motor in the sequence stops.

Using a rotational frequency of 80 Hz as indicated above, each motor is hence able to carry out 4 revolutions within each actuation time window of 50 ms, i.e. four vibrations by each motor at a time. Following the working period of 60 seconds, the operation is halted for 5-10 seconds, and after 6 such full cycles, a longer break of 30 seconds, for example, is taken.

A second exemplary operating scheme following the same main steps as shown in FIG. 3 may be that motor A on the first run is allowed to operate for 150 ms (i.e. 12 vibrations), after which motor B is started for the first time at time 250 ms and runs for 150 ms to time 400 ms. Motor C is then started 100 ms later, i.e. at time 500 ms, and runs for 150 ms to time 650 ms. 100 ms later, that is, at time 750 ms, motor A is started for the second time and runs for 150 ms to time 900 ms, and 100 ms later, that is, at time 1000 ms=1 s, motor B is started for the second time—and so on in such cyclic sequence.

This sequence is, as it appears, slower than the sequence described first, and a break occurs between each motor run. In the first scheme, it is switched between the motors as much as 12 times per second, whereas in the second scheme, switching occurs 4 times per second. The pulse sequence may be repeated 20 times, i.e. for a time period of 15 seconds, before a longer break of 3 seconds, however with an even longer break of 10-15 seconds being taken following 1 minute of operation.

The programming of the electronic control circuit is carried out according to experiments in order to use a sequencing to which most users will respond positively. However, possibilities are also envisioned for producing units having differently programmed control circuit boards, or, in the most advanced case, options for user selection of program.

When having more than three vibrator units 8 in the vibrator row 14, an adapted scheme is run that traverses the individual vibrators repeatedly and cyclically, with or without a short break at the transition from one vibrator to the next and with a longer break following a predetermined working period of 1 minute, for example.

When using more vibrator rows as discussed above, the operating scheme is extended. If the vibrator rows are all equal, it is possible to run e.g. three rows entirely simultaneously and in the same manner. However, a certain time delay between the upper row and the two rows on the sides could be more advantageous. In other respects, there are no restrictions on the kind of operating scheme selected.

As mentioned above, there may also be provided a means for controlling the intensity of the operating scheme in dependence of signals from an integrated heart frequency sensor. In this manner, the duration of breaks, for example, may be extended if the heart rate of the user increases to a higher than desirable level.

The functions and schemes discussed herein may be easily incorporated in an appropriately sized circuit board for integration together with a number of micro vibrators and a miniature battery in a mounting attachment such as discussed above. Electronic, programmable micro circuits are currently well-established technology.

Also, established methodologies exist for embedding and casting together of such elements as mentioned herein, e.g. in a rubber material in the form of rings or condom implementations.

Due to the wave cycle of the motor row, the arrangement produces a pumping effect on arteries and veins in the penile body that both increases the flow of blood to the sponge bodies of the penis and reduces the backflow. In combination, these effects provide for a more powerful erection.

Advantageously, the invention may be designed with an internal bulb applying pressure against the upper side of penis to further limit the backflow of blood through veins 4 (see FIG. 1).

With no restrictions, the erection enhancement means of the invention is susceptible to various embodiments, e.g. implemented as a tightening ring or mounted as a plaster or adhesive tape. Other implementation alternatives may be as a sleeve or as a clamp. It may also be mounted within a vacuum pump.

Clinical experiments have been carried out in order to study the effect of the present invention, and to find out which operating schemes provide satisfactory or less satisfactory results. A number of parameters may be varied, and there is still need for further testing. However, the operating schemes reported herein seem to give a satisfactory effect.

The effect is measured using the well-established "RigiScan" measuring methodology, which is well known for the man skilled in the art.

Numerous different combinations of pulse length, pulse occurrence rate, and break periods yields good results. Seemingly recommendable pulse lengths are in the range of 50-250 ms (which with a motor rotation frequency of 80 Hz results in four to twenty vibrations per pulse). Well-working pulse rates are in the range of 2-10 pulses per second. Pauses between the individual pulses may be varied in the range of −10-100 ms (i.e. the delay from the time when a motor in the row stops to the time at which the next motor starts). The pauses used will be short breaks of down to 3 seconds as well as longer breaks of up to 60 seconds. Any combination of shorter breaks and longer breaks may also be used. Working or running time (consisting of pulses and breaks) may be varied within the range of 10-60 seconds.

Within one and the same operating scheme it is also possible to change some of the parameters described above, in operation. Continuous variation of the occurrence rate and length of breaks, based on incoming measurements of the heart rate of the user, has been mentioned above. It is also possible to counteract a tendency to "numbness" caused by monotonous action, by altering the motor pulse rate e.g. from 4 per second to e.g. 10 per second from one sequence to the next, i.e. at the point of an intermittent short break of 3 seconds, for example, and then back again after the next short break.

The effect of the present invention may, in special cases with a need of orgasm/ejaculation for disabled patients (especially when there is a full breakage in the nerve connections to the abdominal area), be boosted by adding additional, individual vibrator motors at the edge of the glans penis. This may e.g. be provided for in a sleeve or condom type of embodiment, or perhaps in a plaster embodiment. In that case preferably an additional vibrator motor is provided on each side, symmetrically along the underside of the glans penis. The powering of such motors then occurs as part of the sequenced pulsation discussed above, e.g. synchronously with, or with a fixed time delay after the sequences for vibrator rows on the sides of the penis shaft.

Piezo Foil Strip Embodiment

Based on the knowledge that it is also possible to assist in generating or enhancing an erection with the use of higher frequency mechanical vibrations, cf. WO 01/70150 A1 and WO 2004/110320 A1, for example, which both show the use of a piezoelectric foil, the inventors have also looked at the effect of using a combination of vibrator rows as discussed above and allocated piezo foil strips.

Figure 4:
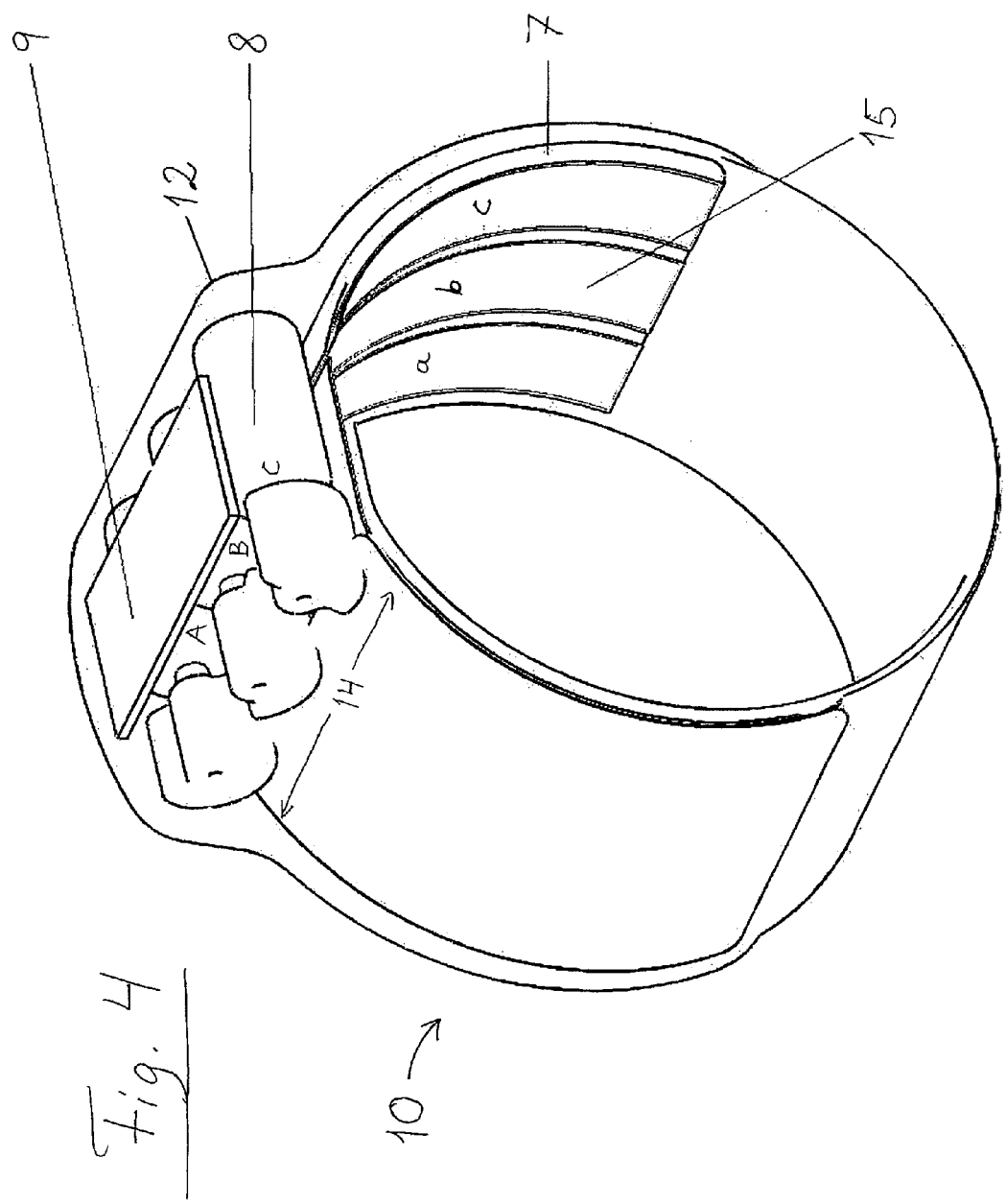
FIG. 4 shows a more sophisticated embodiment of the means according to the present invention.

Turning to FIG. 4, which in most respects shows the same embodiment of the invention as FIG. 2, but in which reference number 15 refers to piezo strips extending downwardly on the inside of mounting attachment 10, and wherein each strip is allocated to a respective one of the three vibrators 8. The piezo foil strips 15 extend downwardly in a similar manner also on the opposite inner surface of ring 10, i.e. three elongate strips 15 a, b, c are located right underneath a respective vibrator. (In another embodiment, with five vibrators 8, for example, there would be five similar piezo strips 15. Also, with three vibrator rows, for example, as indicated above, there would be two alternative arrangements of piezo foils: Arrangement 1 would exhibit the same piezo foils as used with only a single vibrator row, i.e. the configuration shown in FIG. 4, but have an additional two vibrator rows on the sides. Arrangement 2 would exhibit three rows of vibrators with allocated, and then correspondingly shorter, foil strips to each individual vibrator, with the strips extending in the same circumferential direction as shown in FIG. 4, i.e. "FIG. 4 strips" cut crosswise into nine strips.)

The underlying piezo strips 15 *abc* are intended to be run synchronously with the operation of vibrator motors 8 ABC in order to further enhance the effect. Therefore, working periods are run simultaneously for the motor system and piezo foil strip system.

The motivation for combining the two different types of vibration is to use a high frequency mechanical "carrier wave" from the piezo foils in order to promote and enhance the effect of the vibrator units. Indeed, some kind of synergy seems to exist, at least when using carefully chosen operation parameters for the vibrators and foils, as it has been found through clinical experiments that the effect on the ability to achieve an erection could be stronger when combining piezo foils and vibrators, than the "sum of the two individual effects."

We will describe a simple implementation of the combination, namely such an embodiment as shown in FIG. 4. It should be noted that while the piezo strips 15 *abc* are shown to extend downwardly by the same length as the (paper) battery 7, this does not need to be the case. However, as mentioned earlier, it is the intention to maintain a lower area of ring 10 free of equipment, so that the elastic material in the lower area is able to expand to accommodate the change of the circumference of penis on an increasing erection, generally from a diameter of about 20 mm to about 60 mm.

Figure 5:
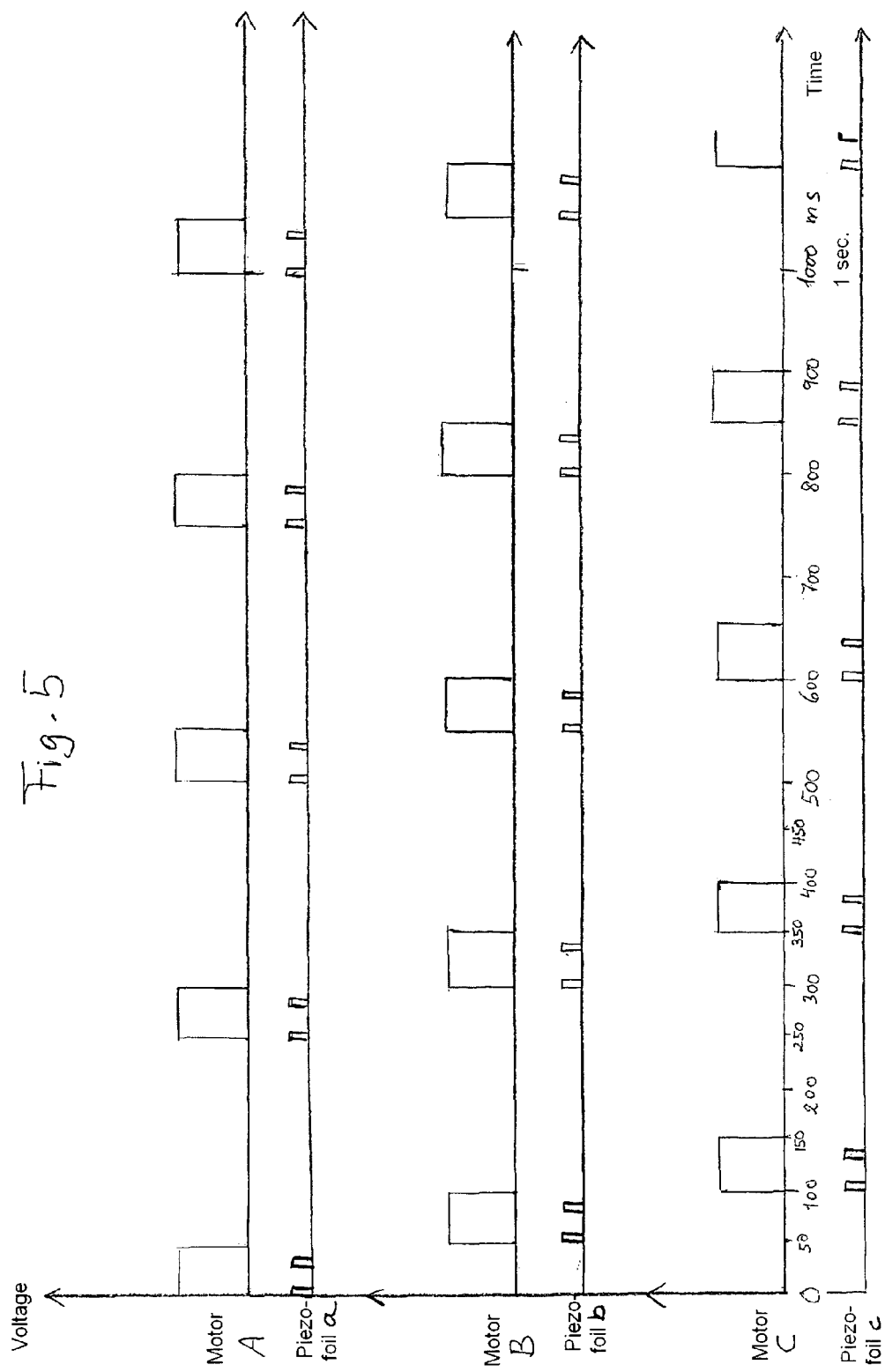
FIG. 5 shows an exemplary operating scheme for use by the means shown in FIG. 4.

An exemplary operating scheme appears in FIG. 5. FIG. 5 is based on FIG. 3 and shows the exact same operating scheme for the vibrator units as does FIG. 3. In this case however, separate lines have been added in order to show an exemplary operation of the piezo foils, and the scheme for foil a is shown right underneath vibrator motor A, etc. Note that while the motor diagrams show the voltage history, i.e. DC voltage as a function of time, the foil diagrams only show the actuation period. What really takes place for the foils is the following:

In a first example, an AC voltage at 4000 Hz (or a frequency in the range of 2000-10000 Hz, preferably in the range of 3000-5000 Hz) is used to excite the foils. The AC voltage is applied to the foils in short impulses, and the first impulse starts at time 0 and is conducted to foil a, shown as a first, erect bar in the diagram right underneath the first pulse to motor A. Thereafter the impulses continue with an impulse occurrence rate of 40 Hz, meaning that two such impulses are discharged within the duration of the first pulse to motor A.

Then the impulses are transferred to foil b in synchronization with the first pulse to motor B, after which the AC impulses continue to follow the motor pulses synchronously, and in the diagram shown, throughout a time period of 1 second.

In the example shown, the duration of each impulse is 10 ms, meaning that the piezo foil is subject to 40 oscillations per impulse (when the fundamental frequency is 4000 Hz). The first impulse occurs at 0 ms, impulse no. 2 at 25 ms (these two being conducted to foil a), impulse no. 3 at 50 ms, no. 4 at 75 ms (these two being conducted to foil b), etc.

All parameters in question may take other values. The fundamental frequency, impulse duration, break between the impulses, and impulse rate, may all be varied within certain limits. For example, the fundamental frequency should be in the range of 150 Hz-3 MHz, as mentioned above. The impulse rate could be in the range of 20-200 Hz, the impulse duration in the range of 5-20 ms, and the break in the range of 10-40 ms.

Thus, in the same manner as for motors 8, foil strips 15 are actuated in a "continuous" wave motion from a to c. So, during a working period of 60 seconds, a sequenced pulsation of the three motors takes place, synchronously with the sequenced pulsation of the underlying foil strips. When the number of motors/motor rows increases, the number of foil strips to be run/controlled synchronously and with corresponding variable parameters increases.

In the same manner as mentioned above:

In order to avoid a potential "numbness" in the penis nerve fibers and sensitive tissue which one aims at activating, it may be of interest to vary the sequences also when piezo foils are used. This may be accomplished, for example, by varying the frequencies applied to the foil strips and motors. In addition, it is possible to vary the time of actuation/de-actuation of foil strips/motors in order to create variations in the stimuli to which the nerve fibers are exposed. The application of homogenous signals for extended periods of time may cause the nerves to "adapt" and to a lesser extent respond to continued stimuli of the same type.

Thus, in a second example, tests have been conducted wherein several fundamental frequencies for the piezo foil were run in sequence:

I) 200 Hz for 1 minute
II) 4 kHz for 1 minute
III) 2 MHz for 1 minute

In these tests, the foil amplitudes were in the range 10-25 μm and the vibrator motors were run at 80-120 Hz. The duration of each pulse A, B and C to the motors and impulses a, b and c to the piezo foil were 1 second to each motor and its corresponding foil, followed by a pause of 300 ms. This sequence of 3.3 seconds was repeated for about 1 minute before changing the fundamental frequency of the foil in the sequence I, II, Ill, I . . . . The test showed that this sequence was significantly more effective than the one described in the first example, maintaining erections without other stimuli.

In an important embodiment of the invention, in adaption to the requirements of some health authorities, outer wings/lugs 16 are integrally cast onto the erection enhancement means as shown in FIG. 6, in order to enable a rapid removal of a penis ring when necessary.

The motivation behind the selected (preferred) parameter value ranges being used is knowledge of the anatomical conditions and the natural activities in connection with normal coitus positions, resulting in "natural" vibration frequencies generated by friction between the female and male skin and pellicle features in the carrying out of such activities. These are conditions inherited in people from a relatively early stage of development, and that make "the body recognize as positive stimulation" frequencies that resemble the natural frequencies.

The invention claimed is:

1. A male sex organ erection enhancement method, comprising:
   placing a substantially cylindrical mounting attachment with vibrator motors on the sex organ, wherein the vibrator motors on the mounting attachment are driven by an electric power supply arrangement;
   driving the vibrator motors, wherein the vibrator motors are arranged in at least one axially straight row with at least three vibrator motors in the row, in sequential pulsation by an electronic control circuit in an amount sufficient to effect, enhance, and maintain an erection.

2. The method of claim 1, wherein the power supply arrangement is a battery positioned on the mounting attachment.

3. The method of claim 1, wherein the vibrator motors are driven in sequential pulsation by the electronic control circuit located on the mounting attachment.

4. The method of claim 1, further comprising:
   operating the vibrator motors, which are three in number and arranged in a single row on the mounting attachment so as to be positioned one after another along the upper side of the sex organ, in a sequence in which the rear motor is run in a first pulse, after which the middle motor is run in a second pulse, and then the front motor is run in a third pulse; and
   repeating this pulse sequence a fixed number of times followed by a longer break.

5. The method of claim 1, further comprising operating the vibrator motors in periods of 15-60 seconds, and with breaks with a duration of 3-60 seconds between the periods.

6. The method of claim 1, further comprising:
   measuring a heart rate with a heart rate sensor integrated into the mounting attachment; and
   adjusting the duration of the breaks and the speed of the motors based on the measured heart rate.

7. The method of claim 1, further comprising:
   measuring an erection strength with an erection sensor integrated into the mounting attachment;
   adjusting the duration of the breaks and the speed of the motors based on the measured erection strength.

8. The method of claim 1, further comprising operating three rows of at least three vibrator motors with the electronic control circuit, with pulse sequences for each row being run in a fixed programmed time relation to each other, and with a first row extending along the upper side of the sex organ and the remaining two rows extending in parallel with the first row but symmetrically on each side thereof further down the periphery of the sex organ.

9. The method of claim 8, further comprising operating the three rows simultaneously with the electronic control circuit.

10. The method of claim 8, further comprising operating the three rows with a fixed time delay relative to each other.

11. The method of claim 1, further comprising operating piezoelectric foil strips configured to cooperate with respective vibrator motors with the electronic control circuit by supplying AC voltages with frequencies in the kHz range, the piezoelectric foil strips being located beneath respective ones of the motors on the mounting attachment, and extending in opposite directions from the position of the vibrator motors.

12. The method of claim 11, further comprising adjusting the time progress of the AC voltages supplied to the foil strips based on the sequence control of the vibrator motors.

13. The method of claim 11, wherein the AC voltages supplied to the foil strips are given a square shape with a fundamental frequency in the range of 1-15 kHz.

14. A male sex organ erection enhancement device comprising:
   a substantially cylindrical mounting attachment placeable on the sex organ;
   a plurality of vibrator motors attached to the mounting attachment;
   an electric power supply arrangement configured to supply electric power to the vibrator motors;
   an electronic control circuit configured to control the operation of the vibrator motors;
   wherein the vibrator motors are arranged in at least one axially extending straight row comprising at least three vibrator motors in the row; and
   wherein the electronic control circuit is configured to energize the vibrator motors of the rows in sequential pulsation.

15. The device of claim 14, wherein the electrical power supply arrangement is a battery located on the mounting attachment.

16. The device of claim 14, wherein the electronic control circuit is arranged on the mounting attachment.

17. The device of claim 14, wherein the plurality of vibrators is three vibrators arranged in a single row on the mounting attachment so as to be positioned one after another along the upper side of the sex organ, and wherein the electronic control circuit is programmed to operate the rear motor in a first pulse, thereafter the middle motor in a second pulse, and then the front motor in a third pulse, and then repeat this pulse sequence a fixed number of times followed by a longer break.

18. The device of claim 14, wherein the vibrator motors are arranged in three rows including a first row extending along the upper side of the sex organ and a pair of rows extending in parallel with the first row on opposite sides of the first row further down on the periphery of the sex organ.

19. The device of claim 14, wherein the mounting attachment comprises a penis ring made of an elastic material.

20. The device of claim 19, wherein the penis ring is provided with piezoelectric foils configured to cooperate with respective vibrator motors, wherein the foils are powered by the supply of AC voltage from the electronic control circuit, and wherein each foil is positioned beneath a respective vibrator motor and outstretched as a foil strip in opposite directions from the position of the corresponding vibrator motor.

21. The device of claim 20, wherein the penis ring includes a single row with at least three vibrator motors positioned one after the other, and wherein a piezoelectric foil strip is located beneath each motor, extends both ways down on the inside of the penis ring and is terminated so that a foil free area is provided on the lower part of the ring, wherein the foil free area is elastic and is configured to accommodate a diameter change of the penis ring from about 20 mm to about 60 mm.

22. The device of claim 14, wherein the mounting attachment includes a pulse sensor configured to measure the current heart rate from pressure variations of the blood flow in the sex organ, and wherein the electronic control circuit is pre-programmed with algorithms to take into account the captured heart rate through the introduction of adapted breaks and motor speed in the operation of the vibrator motors.

23. The device of claim 14, wherein the mounting attachment includes an erection sensor configured to measure the erection strength, and wherein the electronic control circuit is pre-programmed with algorithms to take into account the measured erection strength through the introduction of adapted breaks and motor speed in the operation of the vibrator motors.

* * * * *

UNITED STATES PATENT AND TRADEMARK OFFICE
CERTIFICATE OF CORRECTION

PATENT NO.        : 8,628,466 B2                                                     Page 1 of 1
APPLICATION NO.   : 13/129701
DATED             : January 14, 2014
INVENTOR(S)       : Orten et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 190 days.

Signed and Sealed this
Twenty-second Day of September, 2015

Michelle K. Lee
*Director of the United States Patent and Trademark Office*